United States Patent [19]

McDonald

[11] 3,937,213

[45] Feb. 10, 1976

[54] BODY FLUID COLLECTION DEVICE

[76] Inventor: Bernard McDonald, 7700 Seville Ave., Huntington Park, Calif. 90255

[22] Filed: June 29, 1973

[21] Appl. No.: 375,012

[52] U.S. Cl. .............. 128/2 F; 23/292; 128/DIG. 5; 128/DIG. 28; 128/275; 128/276
[51] Int. Cl.² .......................................... A61B 5/14
[58] Field of Search ............ 128/2 R, 2 F, 275, 276, 128/272, DIG. 5, DIG. 28, 214 R, 214.2; 195/127, 139, 103.5; 23/292, 258.5; 259/110, 99, 10; 4/258, 267, 274, 278; 73/421 R, 421 A, 421 B, 425.6, 425.4; 215/6, 216, 250, DIG. 3; 206/219

[56] References Cited
UNITED STATES PATENTS

| | | | |
|---|---|---|---|
| 739,283 | 9/1903 | Bonney | 259/99 |
| 774,350 | 11/1904 | Castle | 99/246 |
| 1,167,273 | 1/1916 | Colling | 4/278 |
| 1,774,258 | 8/1930 | English | 128/DIG. 28 |
| 2,333,684 | 11/1943 | Schwab | 206/438 |
| 2,461,558 | 2/1949 | Meagher | 206/364 |
| 2,527,992 | 10/1950 | Greenberg | 128/272 UX |
| 2,832,344 | 4/1958 | Davidson | 128/DIG. 5 |
| 2,848,999 | 8/1958 | McGrew et al. | 128/DIG. 5 |
| 2,955,595 | 10/1960 | Semple | 128/214 D |
| 3,074,402 | 1/1963 | Broman | 23/258.5 |
| 3,079,919 | 3/1963 | Harrison et al. | 128/272 |
| 3,187,750 | 6/1965 | Tenczar, Jr. | 128/272 |
| 3,328,255 | 6/1967 | Ilg | 128/214 D |
| 3,405,706 | 10/1968 | Cinqualbre | 128/DIG. 5 |
| 3,467,095 | 9/1969 | Ross | 23/258.5 X |
| 3,494,351 | 2/1970 | Horn | 128/2 F |
| 3,518,164 | 6/1970 | Andelin et al. | 128/2 F X |
| 3,720,524 | 3/1973 | Nakagami | 215/6 X |

*Primary Examiner*—Kyle L. Howell
*Attorney, Agent, or Firm*—Christie, Parker & Hale

[57] ABSTRACT

A technique is provided for collecting and transferring body fluids such as blood or sputum. A blood sample is taken through a tube into an evacuated chamber. After the sample has been drawn it may be centrifuged to separate red cells from the plasma. Samples are then withdrawn from the first chamber into a second evacuated chamber where several analysis tubes are located. The sample is thus subdivided for analysis without exposure of the sample to the person making the tests. In another embodiment sputum is collected in a first chamber and is first blended with a preservative and then transferred to a second chamber where analysis tubes are located. Transfer is likewise without exposure of the person or contamination of the sample.

25 Claims, 4 Drawing Figures

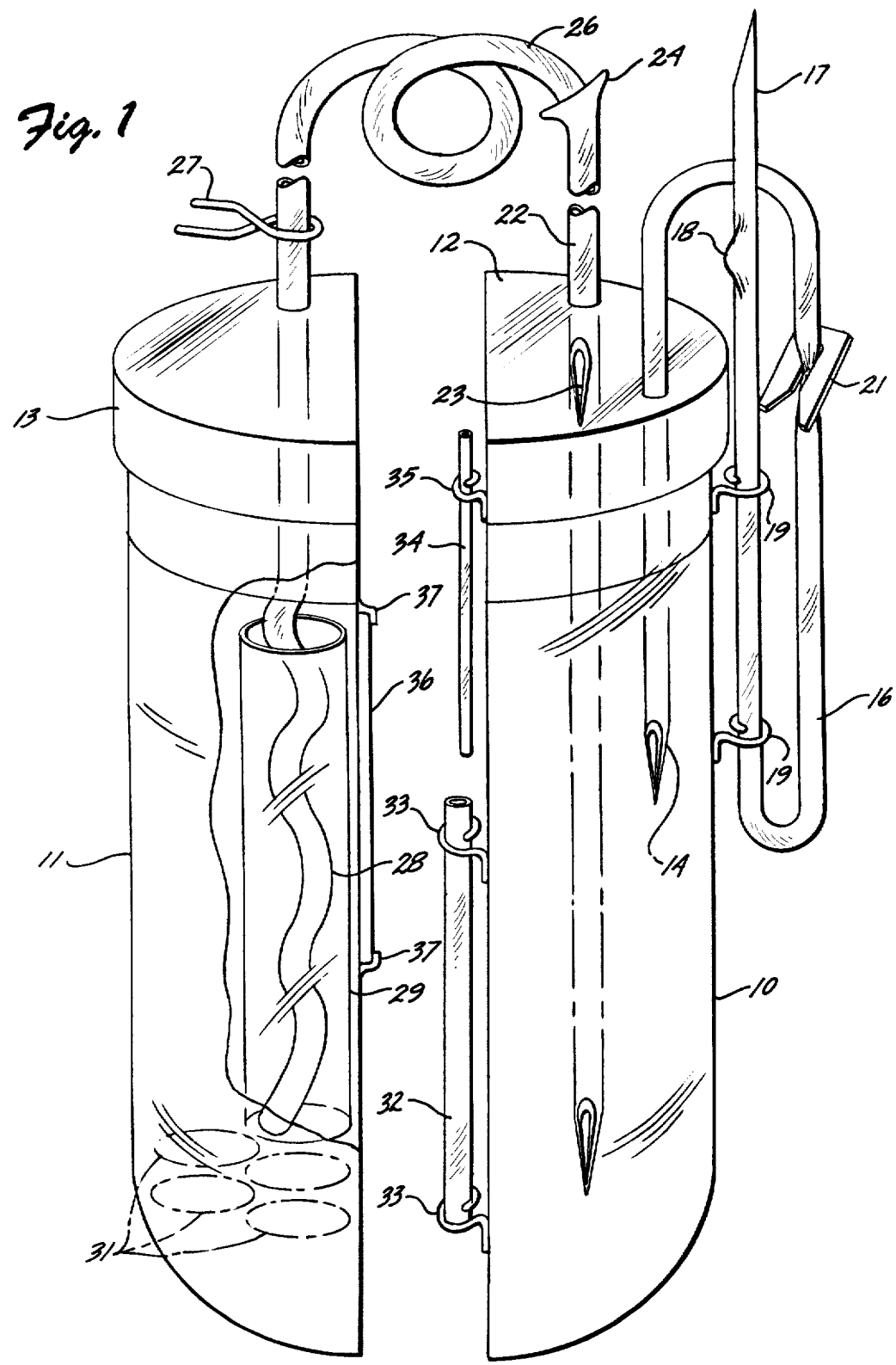

U.S. Patent   Feb. 10, 1976   Sheet 2 of 2   3,937,213
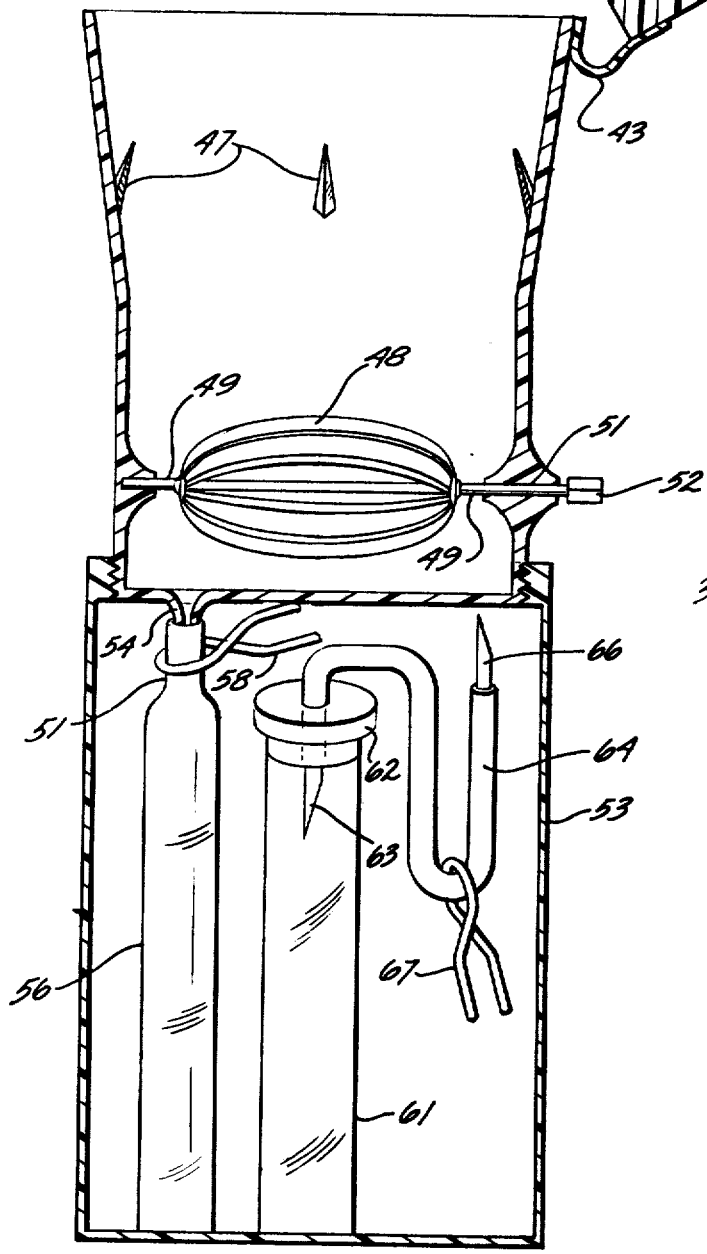
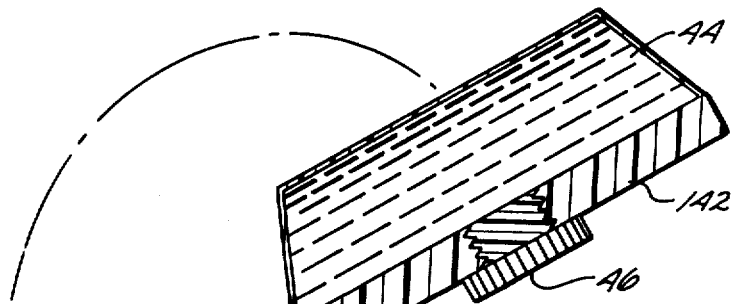
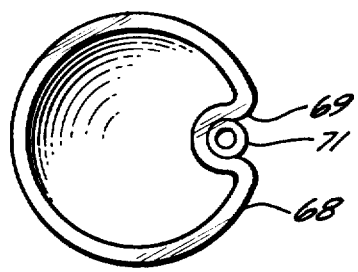
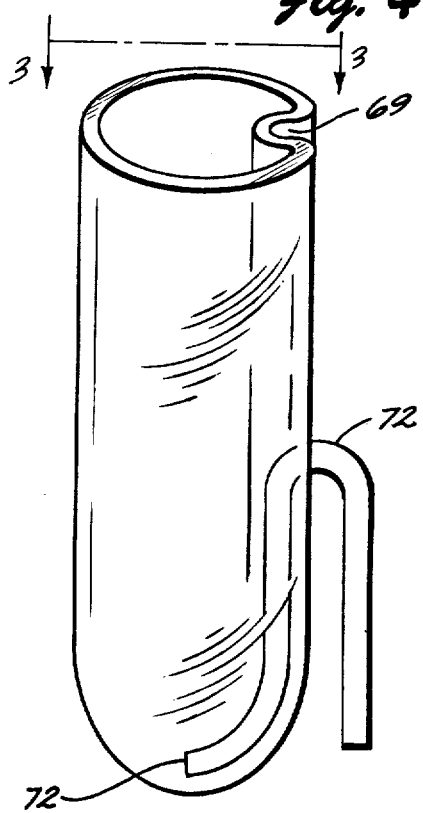

BODY FLUID COLLECTION DEVICE

BACKGROUND

Very commonly samples are taken of a patient's blood for laboratory tests. This blood is obtained from the patient's veins by means of a hypodermic needle inserted into a suitable superficial vein which has been previously distended by means of a tourniquet. The required quantity of blood is drawn into the syringe by pulling on the barrel of the instrument.

More recently the conventional syringe has been paritally replaced by a technique employing a series of preevacuated containers. When such a system is used, a single needle penetrates the vein and a series of evacuated containers are sequentially connected thereto for drawing a number of blood samples for different analyses. The individual containers are advantageous since they are disposable and presterilized and can secure consistent blood volume.

Such an arrangement can have problems, however, since the angle of vein penetration is sometimes awkward when the container is large. In some instances the puncture needle has been placed eccentrically on the container to minimize this problem. When the individual preevacuated containers are changed there is a significant chance that the puncture needle will be displaced or will penetrate the opposite wall of the vein. In either case this necessitates an additional puncture and often results in hematoma formation. The condition of the patient's vein and the skill of the operator are important factors in determining whether this may occur.

In addition, the preevacuated collection tubes often contain a substance such as anitcoagulant or blood preservative which can have significant adverse effects on the patient if it is aspirated into the patient's bloodstream. Such could happen, for example, if the container has developed a leak and the vacuum has been lost. This condition cannot be ascertained by simple inspection and careless work on the part of the person taking the sample could lead to undesirable toxic substances entering the patient's bloodstream.

Ordinarily when blood samples are taken, analysis is made on whole blood and on blood that has been centrifuged to yield plasma, serum, buffy layer and red cells in separate fractions. It is desirable to provide a technique for safely and quickly collecting blood from the patient, separating blood into the desired fractions, and possible initiating analysis within a closed system without exposure of the sample to the outer environnment. This serves to protect personnel from contamination and preserve the blood from external contamination.

Another diagnostic technique that is sometimes used, particularly for detection of respiratory diseases such as tuberculosis and cancer, is the collection and examination of sputum. The current collection technique has the patient cough and expectorate into a jar which is then sealed with a cardboard lid or screw on cap. In the laboratory the technician transfers the sample to suitable analysis devices. This technique is not only inefficient but is hazardous to the examiner. The hazard is compounded in the laboratory when the technician picks out portions of the sputum and smears it onto a glass slide or innoculates a bacteriological culture. Ordinarily this operation is carried on in an open environment or at best under an exhaust hood. In addition to the hazard to the technician, the operation is esthetically unpleasant because of the nature of the sample and consequently it is often rushed and poorly performed.

The detection of cancer cells in sputum offers the greatest potential for discovery in a curable stage. Unfortunately the technique is disappointly unsuccessful. A major impediment to the detection of cancer cells is the natural high viscosity of the sputum which prevents concentration of cellular elements by sedimentation or centrifuging. Attempts to employ a mucolytic substance have been thwarted by the fact that any such substance which will effect liquefaction of mucus generally also damages or destroys the cells that are sought.

The best technique has been to add 50% isopropyl alcohol to sputum and then mix in a common household blender. The blender must be cleansed thoroughly after each individual sputum sample which is very time consuming. In addition, the technique is carried out in an open system so that it is hazardous to laboratory personnel.

Another technique is to place the sputum on absorbent paper and pick out blood or purulent specks with forceps. Again, the hazards of this, as well as the unpleasant nature, are apparent and it is little wonder that cytotechnicians are not enthusiastic about preparation of sputum by any of the current methods.

It is, therefore, desirable to provide a sputum collection and sampling technique which can be accomplished with disposable elements and in a substantially closed environment which minimizes exposure of the sample to contamination and exposure of the technician to the sample.

DRAWINGS

These and other features and advantages of the present technique will be appreciated as the same becomes better understood by reference to the following detailed description of a presently preferred embodiment when considered in connection with the accompanying drawings wherein:

FIG. 1 illustrates semi-schematically in perspective a blood collection device constructed according to principles of this invention;

FIG. 2 illustrates in longitudinal cross-section a sputum collection and analysis device constructed according to principles of this invention; and FIGS. 3 and 4 illustrate in top view and perspective view respectively a centrifuge tube particularly useful for such analyses.

DESCRIPTION

FIG. 1 illustrates in perspective a blood sampling unit constructed according to principles of this invention. Although described primarily for taking of blood samples it will be apparent that other biologic fluids may be sampled and the sample divided into aliquots for analysis by using such a device. Thus, the fluid in abscesses, peritoncal cavity, pleural cavities, spinal columns, and the like can also be sampled and handled in a device as hereinafter described.

As illustrated in FIG. 1 the device comprises a pair of containers 10 and 11 each of which is in the form of an open top semi-cylinder with a rounded bottom. The first container 10 is referred to hereinafter as a collection container and the second container 11 is referred to as a sample container. Each of the containers is closed by a rubber stopper, 12 and 13 respectively, having a generally semi-cylindrical form conforming to the respective container. The stoppers seal the containers so that vacuum is maintained therein until the device is ready for use.

A hollow needle 14 pierces the stopper 12 in the collection container 10. The needle is tubular in a conventional manner for passing fluids therethrough. A relatively short flexible tube 16, sufficiently impervious to air to maintain the vacuum within the container, is connected to the needle 14. At the opposite end of the flexible tube 16 is a second hollow needle 17 including an enlarged portion 18 or other suitable means for gripping and applying force along the length of the needle. The flexible tube 16 and needle 17 are preferably connected to the collection container 10 by flexible clips 19 which keep them in position until ready for use.

Since the hollow needles 14 and 17 and tube 16 would permit air to leak into the evacuated container 10, a clamp 21 is provided on the flexible tube. Any of a variety of conventional clamps may be used for sealing the tube to prevent air leakage. A simple plastic clip with generally V-shaped groove that can be pressed onto the tube provides an inexpensive and effective seal. A spring wire clip that clamps the tube and is easily released by finger pressure is also suitable. Various inexpensive cam and roller clamps have also been developed for clamping medical tubing and are suitable for practice of this invention.

A second hollow needle 22 has its tip 23 embedded into the rubber stopper 12 so that the hollow needle is sealed. An enlargement 24 on the needle permits it to be manipulated so that the tip can be pressed through the stopper at a desired time after a sample has been collected in the container 10. The needle 22 is sufficiently long that the tip 23 can be brought to the bottom portion of the collection container, as seen in phantom in FIG. 1. A flexible transfer tube 26 is connected to the needle 24 and extends (either directly or by way of a rigid portion) through the second rubber stopper 13 into the sample container 1. It will be apparent that although the tubes 16 and 26 are flexible so that they can be bent, the wall thickness is sufficient that the vacuum therein does not cause the walls to collapse. A releasable clamp 27 closes off the tube 26 to prevent fuid flow therethrough until desired.

On the end of the tube 26 in the sample container 11 there is a somewhat enlarged plastic tube 28 which is sufficiently flexible that the walls may collapse under low forces. When the blood collection device is packaged and ready for use the interior of the tube 28 is evacuated as well as the surrounding space in the sample container 11. In this condition the walls of the flexible tube 28 are normally collapsed and the tube simply hangs flacid within the container. Since it is flacid and the walls can be fairly readily collapsed it may be desirable to provide some mechanical support for the tube. There is, therefore, provided a glass or rigid plastic tube 29 surrounding the principal flexible portion of the collapsible tube 28.

In the embodiment illustrated in FIG. 1 there is illustrated one needle 22 connected by a flexible transfer tube 26 to a collapsible sample tube 28 within a rigid test tube-like tube 29. Four additional circles 31 are illustrated in phantom in FIG. 1 and it should be understood that each of these circles indicates the position of an additional sample tube connected by a corresponding flexible tube (not shown) to a corresponding needle (not shown) embedded in the rubber stopper 12 of the collection container. Thus in FIG. 1 portions of the blood collection and sampling device have been deleted to enhance clarity. The additional needles and tubes not shown in FIG. 1 are substantially identical to the assemblage illustrated and hereinabove described.

A small test tube 32 is connected on the exterior of the collection container 10 by any suitable plastic clip 33. In addition a conventional small diameter capillary hematocrit tube 34 is connected to the exterior of the collection container by a suitable clip 35. As illustrated herein the test tube 32 and the hematocrit tube 34 are mounted on the flat side of the semi-cylindrical collection container. Other suitable locations for the tube and means for connecting them will be apparent. A slide 36 is also removably mounted on the flat side of one of the containers by any suitable clips 37. During use a drop of whole blood is placed on the slide to form a smear for microscopic examination.

When the blood sampling device is packaged for use, the entire interior of the two containers 10 and 11 and the tubes 26 therebetween, as well as the portion of the tube 16 before the clamp 21, are evacuated and sealed. The entire assembly is sterilized and packaged in a sterile container or plastic wrapping so as to maintain sterility until used.

When it is desired to use the blood collection device it is removed from its sterile package and the needle 17 is inserted into a superficial vein of a patient in the conventional manner. The clamp 21 is then released so the vacuum in the collection container 10 assists in drawing a blood sample. When a sufficient sample of blood has been obtained in the previously evacuated collection container, the clamp 21 is replaced and the needle 17 withdrawn from the vein.

A portion or all of the flexible tube 16 is removed from the collection container by removing it from the needle 14, or withdrawing the needle 14 through the stopper, or by simply cutting the flexible tube. The end of the tube 16 or attached needle which remains full of blood is touched to an end of the microhematocrit tube 34 so that a sample is drawn by capillary action in the conventional manner. A drop of the whole blood is also put on the slide 36 for microscopic examination. Thereafter the clamp 21 is released and the remaining blood in the tube is drained into the test tube 32 for laboratory use. The bulk of the blood sample obtained is of course still in the initial collection container 10.

Blood is composed of a solid component, namely the red blood cells, platelets, and white cells, and a fluid component or plasma. These components can be separated and depending on the test being carried out it is desirable to select any of three or four fractions of the blood sample. Whole blood is desirable for red blood cell counts, white blood cell counts, platelet counts and erythrocyte sedimentation rates. When whole blood is desired the blood is collected into an anticoagulant substance such as calcium oxalate or heparin. Plasma is sampled for measurement of blood albumin, globulin, fibrinogen, protein electrophoresis and is employed in cross matching of blood. Plasma is the liquid portion of the blood obtained after centrifuging anticoagulated blood. Serum is the fluid left after blood has coagulated. It is essentially plasma without its proteins which remain in the coagulated portion. In addition, it may be desirable for some tests to obtain a sample rich in the so-called buffy layer which remains after centrifuging as a thin layer rich in white blood cells atop the heavier red blood cells.

Due to different concentrations of body chemicals inside the blood cells and outside in the plasma or serum it is essential for most tests to separate the cells from the plasma very quickly after blood has been withdrawn from veins and before the contents of the cells leak out into the plasma.

Each of the collapsible sample tubes 28 in the sample container may include a suitable reagent for making blood analyses. Thus, for example, one of the collapsible tubes 28 may be provided with a small amount of conventional anticoagulant for obtaining plasma samples. If a plasma sample is desired, the needle 22 corresponding to the collapsible tube 28 containing the anticoagulant is pressed through the stopper 12 until its tip 23 is in the whole blood collected. Release of the clamp 27 on the tube 26 leading to the sample container permits blood to flow therethrough and into the collapsible tube until it is turgid.

The vacuum in the sample container 11 implements this transfer of blood from the collection container to the sample container. It will be apparent that vacuum in the collection container 10 must be released before blood will flow therefrom. If the sampling tube 16 is cut off or removed from the needle 14 air pressure is admitted to the collection container and blood will flow therefrom. If the needle 14 is withdrawn from the collection container a similar hollow needle may be inserted through the stopper to admit air.

After a sample has been withdrawn into the sample container for plasma separation the entire device is placed in a conventional centrifuge. For this purpose the slide, test tube and hematocrit tube between the two semi-cylinders are removed for normal laboratory processing. The two semi-cylindrical containers 10 and 11 are placed face to face and inserted into the centrifuge.

After centrifuging the additional needles 22 (not shown) are pushed through the stopper so that the tip thereof reaches into the supernatant serum over the red cells. The tip 23 can be pushed down to a point that permits maximum extraction of serum without distrubing the underlying layer of cells. Further, if desired, one of the needles can be pushed down so that its tip is in and extracts a mixture rich in the buffy coat for maximum concentration of white cells and the like.

After whole blood or serum or buffy layer has been transferred from the collection container to the respective tubes 28 of the sample container, this latter container is opened so that the samples can be removed. These are obtained by simply snipping off the respective tube 28 above the surrounding test tube 29 or if desired a suitable tearing "rip cord" can be incorporated for rapid removal. The tubes with their samples can then be handled according to conventional laboratory techniques or the cutoff portion may be clamped for sealing so that the tubes can be transported or frozen or otherwise stored for later use.

If desired, instead of the flacid collapsible sample tubes illustrated, rigid, pre-evacuated sample tubes can be placed in the sample container which need not be evacuated. Each rigid tube has a rubber stopper perforated by a transfer needle and transfer occurs as hereinabove described. The transfer tube can be made integral with a sealing stopper in such an embodiment. Each tube can contain any desired anticoagulant or other reagent. Some can contain microorganism growth cultures if desired.

The various transfer tubes and associated needles are preferably color coded so that the technician transferring the blood from the collection container to the sample container has little, if any, chance for error. In addition, each of the separable elements of the prepackaged blood collection device are provided with a common serial number so that the opportunities for confusing samples from several patients is substantially completely eliminated.

It will be noted in the preferred embodiment that the collection container 10 does not have any anitcoagulants or other reagents which can inadvertently be aspirated into the patient's bloodstream. Whole blood is drawn into the sample container and if an anticoagulant sample is desired it is transferred from the collection chamber to the sample container after the device has been removed from the patient. This completely avoids the possibility of inadvertent transfer of harmful reagents into the patient's bloodstream, permitting the drawing of blood samples without danger to the patient. The collection container can remain upright during the drawing of the blood sample and the needle 17 that enters the vein can be manipulated separately therefrom due to the flexible connecting tube 16. This makes drawing the sample easier and significantly reduces chances of damage to veins.

For other body fluids, such as pleural effusions, abscesses, fluids in body cavities, and the like, a similar apparatus is employed for initially collecting the fluid sample and subsequently dividing it into aliquots. The sample tubes in the sample container contain reagents suitable for the desired examination. Thus, for example, if desired, the several tubes may include bacteriological culture media for a growth of microorganisms. One of the sample collection tubes may include formalin for preservation of tumor cells. Such an arrangement is particularly desirable for samples of this nature since samples are taken and subdivided without contaminating personnel or exposing the fluid to environmental microorganisms.

FIG. 2 illustrates in vertical cross-section a device for collecting and subdividing samples of sputum. This device is a completely closed system after the sample has been collected and includes means for breaking up the tenacious mucus without cellular damage. This enables the person performing the tests to concentrate substantially all of the cellular contents of sputum so that if cancer, tuberculosis, fungi infections or the like are present, the pathologist can readily detect them. Early detection of lung cancer is particularly important since by the time the lesions are visible on X-ray or the person presents external symptons the chances of cure by present day techniques are slim. The closed system provided in practice of this invention protects technical personnel, removes the usual esthetic repugnance of sputum testing, and minimizes the chances for contamination of the sample.

The sputum collection device has an upper collection container 41 open at the top so that the patient can expectorate into the container. A cover 142 is connected to the collection container 41 by a flexible plastic strap 43. A portion of the cover is hollow and contains a preservative solution 44 such as isopropyl alcohol or the like. A threaded plug 46 is provided in the cap for initial filling or changing of the fixative fluid, if desired. Additional fluid can be added during use of the device, too.

Within the collection container 41 are a plurality of spikes 47 positioned so that when the cover is firmly inserted into the container the chamber containing the fixative liquid 44 is perforated. This causes the fixative to drain from the cover and into the collection chamber to mix with the sputum. Preferably several spikes 47 are located around the periphery of the collection container so that the cover is perforated at several points and the flow of fixative down the walls carried with it sputum that may be present. The cover containing fixative is preferred so that the patient himself, after expectorating into the cup, tightly closes the container and minimizes the possibility of exposure of personnel to material which may be rather dangerous.

A pair of conventional beaters 48 are arranged adjacent the bottom of the collection container on transverse shafts 49. Each shaft is journalled at one end in the wall of the collection container and at the opposite end passes through a combined bearing and seal 51. A square shank 52 on the end of the shaft permits connection to a drive motor (not shown) similar to a kitchen mixer.

After the sputum has been collected and the lid closed to add the fixative, the beaters are actuated to thoroughly mix the fixative with the sputum. This provides a thin emulsion of sputum and fixative in the container and breaks up any mucus that may tend to remain connected. This assures dispersion of the cellular material throughout the fixative for subsequent separation. It is found that such mechanical mixing with a suitable low viscosity fixative is the only way to assure a high yield of intact cellular material.

It will be apparent that other mechanical mixing techniques may be employed, thus, for example, the collection container may include rapidly rotatable blades which emulsify the sputum in the same general manner as a kitchen blender. If it is desired to avoid a seal for the mechanical drive means for emulsifying may be included within the container with suitable steel parts or inserts that permit driving in a moving magnetic field. The seals and bearings required for the emulsifying means are not of great criticality since the entire device is used but once and then discarded. Samples other than sputum, such as feces, may also be collected in such a device.

The bottom of the collection container illustrated in FIG. 2 is threaded for connection to a lower sample container 53. Means are provided in the sample container for withdrawing aliquot samples of the emulsion of sputum and fixative. Two such techniques are illustrated in the illustrated arrangement and it will be understood that if desired sample collection tubes like those hereinabove described and illustrated in FIG. 1 may be employed with the entire lower container evacuated. If such an alternative arrangement is employed an intermediate section (not shown) or other means for gaining access to clamps for closing off collapsible tubing are needed.

In one arrangement illustrated in FIG. 2 a short rigid tube 54 extends downwardly through the bottom of the collection container into the sample container. A sample tube 56 is connected to the tube 54. The neck 57 of the sample tube 56 is sufficiently flexible that its walls can be collapsed by a clamp 58, which permits sealing of the interior of the sample tube to maintain a vacuum therein. When the clamp is released the emulsion flows into the sample tube. After the sample has been thus obtained the neck of the sample tube can be cut off and the tube removed for conventional examination.

Alternatively an evacuated sample tube 61 may be included in the sample container without permanent attachment to the collection container. In such an arrangement a rubber stopper 62 seals the sample tube and is perforated by a needle 63. The needle is connected to a flexible tube 64 which has a second needle 66 at its opposite end. A clamp 67 closes off the flexible tube 64 to prevent air from leaking into the evacuated sample tube. When it is desired to take a sample of sputum from the collection container, the bottom of the container is perforated by needle 66. After perforating the bottom the clamp 67 is released drawing a sample into the evacuated tube. When the desired quantity of sample is obtained, the needle 63 can be withdrawn fron the stopper 62 leaving the tube in place suitable clamped off to prevent leakage. Alternatively the bottom of the collection container may be made of suitably flexible material that the hole made by the needle 66 closes when the needle is withdrawn thereby preventing leakage of the emulsified sputum from the collection container.

Either of the sample collection tubes 56 or 61 may be in the form of a special centrifuge tube 68 such as that illustrated in FIGS. 3 and 4. As illustrated in this embodiment the entrifuge tube has a reentrant groove 69 running along at least a portion of its length. A flexible tube 71 has one end 72 inside the test tube 68 right at the bottom. The flexible tube 71 passes through the wall of the test tube and lies in the groove 69. If during the course of taking a sample it is desirable that the centrifuge tube 68 be evacuated a suitably conformed stopper may be provided in the tube or the reentrant groove may terminate prior to the upper end of the test tube so that a circular stopper is suitable. In addition, the free end of the flexible tube 71 should be sealed.

When the centrifuge tube 68 is used the flexible tube 71 lies in the groove 69 and the entire tube is placed in a centrifuge to bring the heavier portions of a sample therein to the bottom. After centrifuging, the flexible tube 71 is removed from the groove and if necessary the end is cut off. The flexible tube can then be lowered to a position such as that illustrated in FIG. 4 so as to drain contents of the centrifuge tube. Since the end 72 of the flexible tube is adjacent the bottom of the centrifuge tube the heavy sediment is withdrawn first and is readily separated from the supernatant without any possibility of mixing as can occur when a pipette is used. It is found that with such an arrangement much better separations are obtained than by decanting or pipetting the contents of the centrifuge tube.

Although limited embodiments of device for collecting body fluids and subdividing the sample into aliquots without exposure of laboratory personnel have been described and illustrated herein many modifications and variations will be apparent to one skilled in the art. It is therefore to be understood that within the scope of the appended claims the invention may be practiced otherwise than as specifically described.

What is claimed is:
1. A body fluid sampling device comprising:
   a rigid collection chamber for initially receiving a complete sample of a body fluid from a patient;
   a rigid sample chamber temporarily connected to the collection chamber;

a plurality of evacuated sample tubes in the sample chamber; and means connected to each sample tube for establishing a selective fluid flow interconnection between the collection chamber and each of the sample tubes, respectively, after collection of the complete sample of body fluid in the collection chamber for dividing body fluid therein into selected aliquots.

2. A body fluid collection device as defined in claim 1 wherein the means for establishing comprises:

a transfer tube having a collapsible wall; and a hollow needle on the tube for entering the collection chamber and withdrawing body fluid therefrom, and wherein at least a portion of the tube is evacuated.

3. A body fluid collection device as defined in claim 2 wherein the collection chamber is evacuated, and further comprising:

a collection tube having a collapsible wall and an end in fluid communication with the collection chamber;

a hollow needle on the other end of the collection tube for withdrawing a body fluid sample from a patient; and means for collapsing the collection tube for maintaining vacuum in the collection chamber.

4. A body fluid collection device as defined in claim 1 wherein the collection chamber and sample chamber each comprise a semicylindrical vessel collectively fittable in a centrifuge and stopper means for sealing each chamber for maintaining a vacuum therein.

5. A body fluid collection device as defined in claim 4 wherein the collection chamber and sample chamber are each evacuated, and the means for establishing comprises a hollow needle having a tip imbedded in the stopper means, a transfer tube having a collapsible wall with one end connected to the needle and the other end connected to one of the sample tubes, and means for collapsing the wall of the transfer tube for inhibiting fluid flow therethrough.

6. A body fluid collection device as defined in claim 5 wherein at least a portion of the sample tubes comprise a plastic tube having a sufficiently pliable wall to collapse in response to a vacuum therein.

7. A body fluid collection device as defined in claim 1 wherein the collection chamber is evacuated and free of analysis reagents and wherein at least a portion of the sample tubes contain a body fluid analysis or preservative reagent.

8. A body fluid sampling device comprising:

a rigid collection chamber comprising a cup-like vessel having an open top and a closed bottom for initially receiving a body fluid from a patient;

a cover for the cup-like vessel;

a rigid sample chamber comprising a second cup-like vessel temporarily connected to the bottom of the first vessel;

a plurality of evacuated sample tubes in the sample chamber; and means connected to each sample tube for establishing a selective fluid flow interconnection between the bottom of the collection chamber and each of the sample tubes, respectively, after collection of body fluid in the collection chamber for dividing body fluid therein into selected aliquots.

9. A body fluid collection device as defined in claim 8 wherein the collection chamber further comprises means for mixing a body fluid therein.

10. A body fluid collection device as defined in claim 9 wherein the means for mixing comprises a pair of mechanical beaters in the collection chamber having a driving end extending through a side wall thereof.

11. A body fluid sampling device comprising:

a collection chamber comprising an open top vessel having a closed bottom for initially receiving a body fluid from a patient;

a sample chamber temporarily connected to the collection chamber;

a plurality of evacuated sample tubes in the sample chamber; and means connected to each sample tube for establishing a selective fluid flow interconnection between the collection chamber and each of the sample tubes, respectively, after collection of body fluid in the collection chamber for dividing body fluid therein into selected aliquots; and a cover on the vessel having an internal closed cavity, said cover including a rupturable portion on a surface inside the collection chamber for establishing fluid flow between the cavity in the cover and the interior of the collection chamber.

12. A body fluid collection device as defined in claim 11 wherein the collection chamber further comprises means for mixing a body fluid therein.

13. A body fluid sampling device comprising:

an open top collection chamber for initially receiving a body fluid from a patient;

a sample chamber temporarily connected to the collection chamber;

a plurality of evacuated sample tubes in the sample chamber; and means connected to each sample tube for establishing a selective fluid flow interconnection between the collection chamber and each of the sample tubes, respectively, after collection of body fluid in the collection chamber for dividing body fluid therein into selected aliquots;

a hollow cover on the collection chamber, said cover including a rupturable portion for establishing fluid flow between the hollow of the cover and the interior of the collection chamber;

a preservative liquid in the hollow cover; and means for rupturing the cover comprising a plurality of points on the collection chamber for cutting the cover as it is inserted in the collection chamber.

14. A sputum collection device comprising;

a rigid cup-like vessel having an open top and a closed bottom;

a sealed hollow cover on the vessel;

a preservative liquid in a hollow in the cover;

means on the vessel for rupturing the cover as it is inserted into the vessel; and means for extracting a portion of fluid from the vessel without removing the cover.

15. A sputum collection device as defined in claim 14 wherein the means for rupturing the cover comprises a plurality of points in the cup-like vessel for cutting the cover as it is inserted into the vessel.

16. A sputum collection device comprising:

a rigid cup-like vessel having an open top and a closed bottom;

a sealed hollow cover for the vessel;

a preservative liquid in a hollow in the cover;

means on the vessel for rupturing the cover as it is inserted into the vessel; and means in the vessel for mixing sputum and preservative liquid therein.

17. A body fluid collection device as defined in claim 16 wherein the means for mixing comprises a pair of mechanical beaters in the collection chamber having a driving end extending through a side wall thereof.

18. A sputum collection device as defined in claim 16 further comprising means for extracting a portion of fluid from the vessel without removing the cover.

19. A blood collection device comprising:
a rigid evacuated collection chamber free of analysis or preservative reagents;
a collection tube in fluid communication with the interior of the chamber and having a collapsible wall;
a blood collection needle on the end of the tube for obtaining a blood sample from a patient;
means for collapsing the wall of the tube;
a rigid evacuated sample chamber containing a reagent; and
means for selectively establishing fluid communication between the collection chamber and the sample chamber for removing a sample of blood from the collection chamber to the sample chamber.

20. A blood collection device as defined in claim 19 wherein the means for establishing comprises;
a transfer tube having an end in the sample chamber and a collapsible wall;
clamp means for collapsing the wall of the transfer tube; and
a hollow needle on the other end of the tube and movable to selectable depths in the collection chamber.

21. A blood collection device comprising:
an evacuated collection chamber free of analysis or preservative reagents;
a collection tube in fluid communication with the interior of the chamber and having a collapsible wall;
a blood collection needle on the end of the tube for obtaining a blood sample from a patient;
means for collapsing the wall of the tube;
an evacuated sample chamber; and
means for selectively establishing fluid communication between the collection chamber and the sample chamber for removing a sample of blood from the collection chamber; and wherein the means for establishing comprises:
a plurality of transfer tubes having an end in the sample chamber and a collapsible wall;
a plurality of clamp means for collapsing the walls of the transfer tubes;
a plurality of hollow needles on the other end of the tubes and movable to selectable depths in the collection chamber; and
a plurality of sample tubes in the sample chamber, each sample tube being associated with a transfer tube.

22. A blood collection device as defined in claim 21 wherein at least a portion of the sample tubes comprise a plastic tube having a sufficiently pliable wall to collapse in response to a vacuum therein.

23. A blood collection device comprising:
a rigid evacuated collection chamber free of analysis or preservative reagents;
a collection tube in fluid communication with the interior of the chamber and having a collapsible wall;
a blood collection needle on the end of the tube for obtaining a blood sample from a patient;
means for collapsing the wall of the tube; and
a rigid evacuated sample chamber and means connecting the collection chamber and the sample chamber for removing a sample of blood from the collection chamber to the sample chamber; and wherein
each chamber is in the form of a semi-cylinder, said chambers collectively forming a cylinder fittable in a centrifuge.

24. A blood collection device as defined in claim 23 wherein the means for removing further comprises a transfer tube having one end in the sample chamber and a collapsible wall; clamp means for collapsing the wall of the transfer tube; and a hollow needle on the other end of the tube movable to selectable depths into blood in the collection chamber.

25. A blood collection device comprising:
an evacuated collection chamber free of analysis or preservative reagents;
a collection tube in fluid communication with the interior of the chamber and having a collapsible wall;
a blood collection needle on the end of the tube for obtaining a blood sample from a patient;
means for collapsing the wall of the tube; and
means for removing a sample of blood from the collection chamber comprising:
an evacuated sample chamber, said collection and said sample chamber each being in the form of a semicylinder, said chambers being collectively fittable in a centrifuge;
a plurality of transfer tubes having one end in the sample chamber and a collapsible wall;
a plurality of clamp means for collapsing the walls of the transfer tubes;
a plurality of hollow needles on the other end of the tubes movable to selectable depths into blood in the collection chamber; and
a plurality of sample tubes in the sample chamber, each sample tube being associated with a respective transfer tube, at least a portion of the sample tubes including a blood analysis or preservative reagent.

* * * * *